(12) United States Patent
Joshi et al.

(10) Patent No.: US 6,419,163 B1
(45) Date of Patent: Jul. 16, 2002

(54) CONTROLLED RELEASE OF SUBSTANCES

(75) Inventors: Ashok V. Joshi; Truman Christian Wold, II, both of Salt Lake City; John Joseph McEvoy, Sandy, all of UT (US)

(73) Assignee: Ceramatech, Inc., Salt Lake City, UT (US)

( * ) Notice: Subject to any disclaimer, the term of this patent is extended or adjusted under 35 U.S.C. 154(b) by 0 days.

(21) Appl. No.: 09/649,565

(22) Filed: Aug. 28, 2000

Related U.S. Application Data

(63) Continuation of application No. 09/028,372, filed on Feb. 24, 1998, now Pat. No. 6,109,539, which is a continuation-in-part of application No. 08/880,124, filed on Jun. 20, 1997, now Pat. No. 5,932,204.

(51) Int. Cl.⁷ .................................................. A61L 9/00
(52) U.S. Cl. .............................. 239/43; 239/37; 239/57; 239/58; 261/104; 261/107
(58) Field of Search .............................. 239/43, 57, 58, 239/37; 261/104, 107, DIG. 88, DIG. 89, DIG. 17

(56) References Cited

U.S. PATENT DOCUMENTS

| | | | |
|---|---|---|---|
| 1,309,820 A | * | 7/1919 | Sherman |
| 2,236,525 A | | 4/1941 | Davis |
| 2,991,517 A | | 7/1961 | Bundy |
| 3,685,734 A | | 8/1972 | Paciorek et al. |
| 3,770,199 A | * | 11/1973 | Hoek et al. |
| 3,804,592 A | | 4/1974 | Garbe |
| 4,312,347 A | | 1/1982 | Magoon et al. |
| 4,339,079 A | | 7/1982 | Sato et al. |
| 4,674,494 A | | 6/1987 | Wiencek |
| 4,809,912 A | | 3/1989 | Santini |
| 4,913,349 A | * | 4/1990 | Locko |
| 4,948,047 A | * | 8/1990 | Zembrodt |
| 5,196,002 A | | 3/1993 | Hanover et al. |
| 5,427,870 A | | 6/1995 | Joshi et al. |

* cited by examiner

Primary Examiner—William C. Doerrler
Assistant Examiner—Christopher S. Kim
(74) Attorney, Agent, or Firm—Factor & Partners

(57) ABSTRACT

The present invention is directed to a device for releasing a volatile substance. The device includes a housing having an interior region, a volatile substance contained within the interior region, and the ability to controllably release the volatile substance from the housing. Such controllable release can be accomplished by the housing being substantially permeable to ambient air, yet substantially impermeable to the volatile substance contained within the interior region of the housing. Additionally, the invention contemplates the use of one or more porous plugs for diffusing the volatile substance therethrough and eventually into atmosphere in a vapor form. To assist such diffusion, the invention likewise contemplates the use of an electrochemical gas generating cell, a heating element and/or other features which allow air to controllably enter into the interior region of the housing.

14 Claims, 6 Drawing Sheets

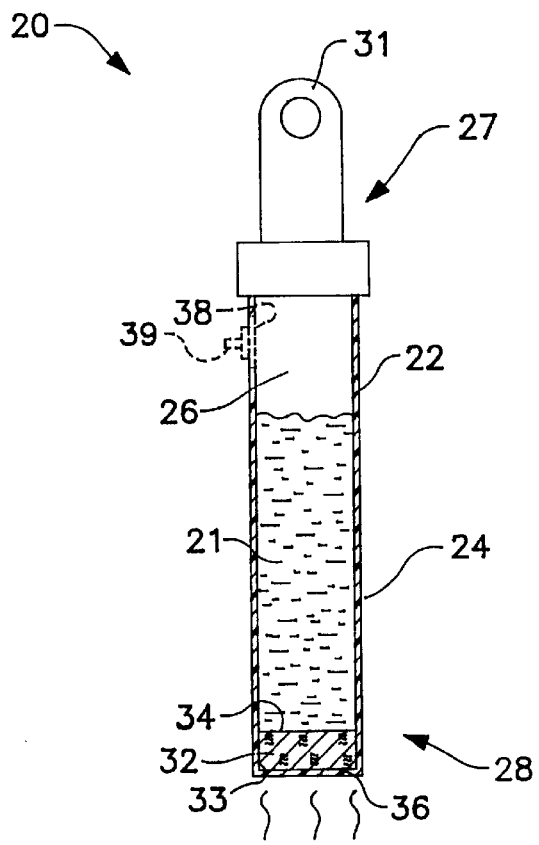
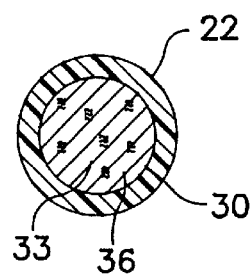
FIG. 1
FIG. 2

CONTROLLED RELEASE OF SUBSTANCES

This is a continuation of U.S. application Ser. No. 09/028,372 filed Feb. 24, 1998 now U.S. Pat. No. 6,109,539 which is a continuation-in-part of U.S. application Ser. No. 08/880,124 filed Jun. 20, 1997 now U.S. Pat. No. 5,932,204.

BACKGROUND OF THE INVENTION

1. Field of the Invention

The present invention relates in general to the release of volatile substances and, more particularly, to a device for controllably releasing volatile substances in their vapor phase to the surrounding atmosphere.

2. Background Art

Devices for delivering volatile substances from a container, as a liquid, to the atmosphere, as a vapor, have been known in the art for several years. In particular, many of these devices make use of the principle of diffusion. For instance, some devices make use of a wick based system. In these systems, one end of a wick is placed in a fluid to be dispensed, while the other end is exposed to the atmosphere. Capillary action forces liquid through the wick and up to the exposed end, where the liquid evaporates off of the end of the wick and into the surrounding atmosphere.

Other devices make use of a gravity driven mechanism, allowing liquids to diffuse through a membrane under the force of gravity. For instance, Zembrodt, U.S. Pat. No. 4,948,047 shows a container for holding a liquid reservoir which is in contact with a membrane positioned in the bottom of the container. Under the force of gravity, the liquid diffuses through the membrane and volatilizes into the surrounding atmosphere from the exposed surface of the membrane. Likewise, Munteanu, U.S. Pat. No. 4,917,301, discloses a similar container for housing a liquid, with a membrane in the bottom of the container. Gravity again forces the liquid to diffuse through the membrane, from where it then evaporates into the surrounding atmosphere.

Although these and other conventional controlled delivery systems have worked well, they have failed to provide for both the controlled and constant release of fluids over an extended period of time. It is a well known goal in the art to increase the linearity of the release of fluids from delivery devices. Moreover, the prior art devices have traditionally been inefficient as they have failed to deliver substantial portions of the fluid contained in the fluid reservoir, thus losing the remaining fluid when it is discarded. Finally, such devices have failed to provide a means for a user to control the rate of release of fluids to the surrounding atmosphere, a desirable feature as different users enjoy different concentrations of the volatilized substance in the air.

SUMMARY OF THE INVENTION

The present invention comprises a device for controllably releasing volatile substances from a housing. The controlled substance release device comprises a housing, a volatile substance, and a means for controllably releasing the substance from the housing. The housing further consists of an interior region, an opening in the bottom end of the device, and means for orienting the device so that the force of gravity maintains the volatile substance over the opening the bottom end of the device.

In one preferred embodiment, the device further consists of a porous plug, which functions as the controlled release means. The plug is positioned within the opening in the bottom of the device, and is in contact with the volatile substance. At the same time, at least a portion of the bottom surface of the plug is exposed to the atmosphere to allow the volatile substance to evaporate from the plug into the surrounding atmosphere. In addition, the device may further consist of a means to re-supply the housing with additional volatile substance. Such a re-supplying means may consist of an independent top end to the device, or an inlet port through which the volatile substance may be poured. Moreover, it is also contemplated that the volatile substance may be contained in a replaceable cartridge having means to cooperate with the housing during use of the device, to, in turn, allow the volatile substance to be released from the cartridge.

In another preferred embodiment, the device further consists of a porous plug and the housing being constructed of a material which is substantially permeable to ambient air, yet substantially impermeable to the volatile substance contained within the housing—in combination functioning as the controlled release means. The housing consists of a series of microscopic pores, and may be fabricated from polypropylene, high density polyethylene, and polyethylene, to name a few. The housing allows ambient air to enter the interior region of the housing, thus allowing the volatile substance to diffuse through the porous plug at a constant and linear rate. At the same time, the housing prevents any loss of the volatile substance from the housing walls, through, for instance, a vent, thus preventing uncontrolled loss of the volatile substance through passages other than the porous plug.

In still another preferred embodiment, the device further comprises a means to control the amount of ambient air that enters the interior region of the housing, thus controlling the release rate of the volatile substance from the device. Such a means consists of a housing that is substantially permeable to ambient air, yet substantially impermeable to the volatile substance, and a shell that obstructs at least a portion of this ambient air permeable housing. The shell may be adjusted relative to the housing to, in turn, control the diffusion rate of the volatile substance through the porous plug and thus the release rate of the volatile substance from the device.

In yet another preferred embodiment, the device further comprises a porous plug and an electrochemical gas generating cell, which act to control the rate of release of the volatile substance from the housing. The cell emits gases into the interior region of the housing, thus allowing constant release of the volatile substance through the porous plug and into the surrounding atmosphere.

In still another preferred embodiment, the device further consists of a first porous plug positioned within the opening in the bottom of the device and at least partially exposed to the ambient atmosphere, a second porous plug positioned in contact with the volatile substance, and an air gap between the two plugs—in combination forming the means for controllably releasing the volatile substance from the housing. In operation, the volatile substance diffuses through the first porous plug and enters the air gap between the plugs in a substantially vapor form. The vapor then diffuses, either remaining in a vapor form or returning to its liquid form, through the second porous plug, before entering the surrounding atmosphere.

In another preferred embodiment, the device further comprises an opening formed in the housing, which is positioned below the volatile substance, and an emanator pad, which is positioned below the opening—the controlled release means in this embodiment. The volatile substance drips through the opening, where it falls onto the emanator pad. The emanator pad, in turn, absorbs the volatile substance, before the substance volatilizes from the surface of the emanator pad into the surrounding atmosphere.

In still another preferred embodiment, the device further consists of a heating element, which increases the evaporation rate, and thus the release rate of the volatile substance.

BRIEF DESCRIPTION OF THE DRAWINGS

FIG. 1 of the drawings is a side elevation view of one embodiment of the device according to the present invention;

FIG. 2 is a bottom plan view of the device according to one embodiment of the present invention;

DETAILED DESCRIPTION OF THE DRAWINGS

Figure 7:
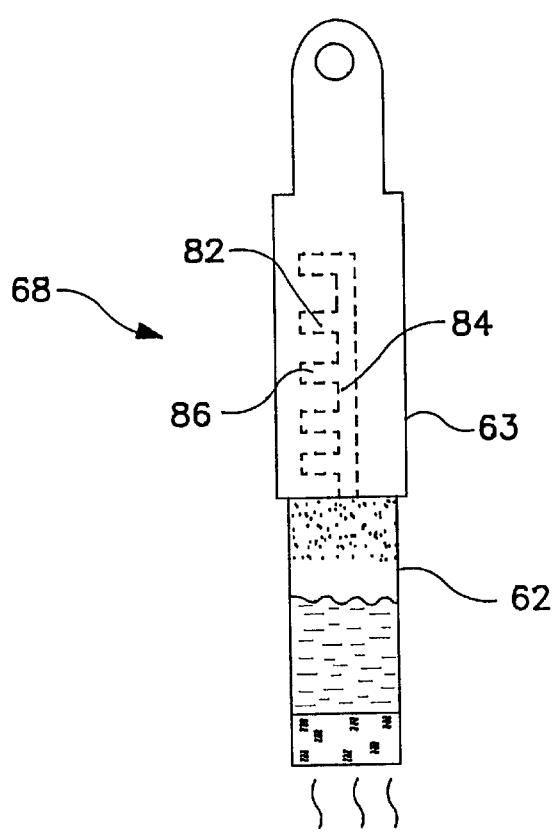
FIG. 7 is a side elevational view of yet another embodiment of the device in which the user controls the release rate.

While this invention is susceptible of embodiment in many different forms, there is shown in the drawings and will herein be described in detail, several specific embodiments with the understanding that the present disclosure is to be considered as an exemplification of the principles of the invention and is not intended to limit the invention to the embodiments so illustrated.

Controlled substance release device 20 is shown in FIG. 1 as comprising volatile substance 21, housing 22, and means for controllably releasing the substance from the housing. The volatile substance is contained within the housing and may consist of any substance exhibiting diffusive properties, such as liquids, vapors, or gelatinous materials. Specifically, the volatile substance may take the form of a liquid from the group including, but not limited to, perfumes, pesticides, insect repellents, air fragrances, medicines, or combinations thereof.

Housing 22 consists of outer surface 24, interior region 26, top end 27, bottom end 28, opening 30 (in the bottom end), and means for controllably releasing the substance from the housing which, in the embodiment of FIG. 1, comprises porous plug 33. In this embodiment, top end 27 further consists of means 31 for orienting the device so that the force of gravity maintains the volatile substance over opening 30 in bottom end 28 of the device. Such an orienting means may consist of a hook, although other means not necessarily associated with the top of the device, such as a stand, Velcro™, etc. are also contemplated.

Also, in a preferred embodiment, top end 27 may be constructed independently of housing 22, so as to allow secured attachment of the top end to the housing and removal of the top end for re-supplying the housing with additional volatile substance 21. To facilitate such removal, while also maintaining a fluid tight seal, it is preferred that the top end is threadably attached or snap-fit to the housing. In the alternative, an inlet port 38 may be positioned in the housing to allow the housing to be re-supplied with the volatile substance. Preferably, such an inlet port also includes a removable sealing member 39, such as a stopper, cap, or threaded plug, which is impermeable to the volatile substance.

Figure 3:
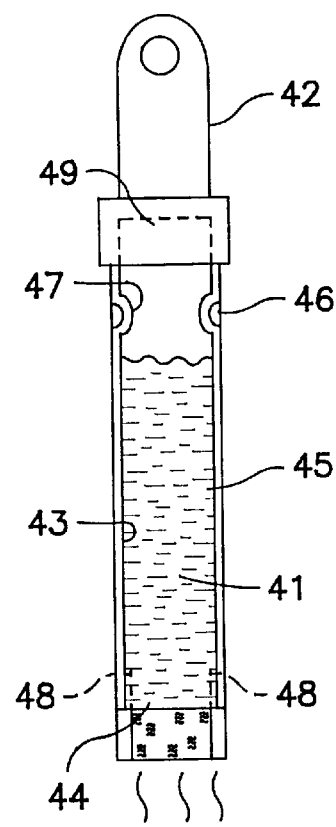
FIG. 3 is a side elevational view of an embodiment of the device in which the volatile substance is contained in a replaceable cartridge.

Alternatively, and as is shown in another preferred embodiment in FIG. 3, volatile substance 41 may be contained within a replaceable and disposable cartridge 45. Such a cartridge may, for example, be held in the housing by a removable cap, or locked into the housing by a snap-fit fastening mechanism such as ridge 46 and groove 47. Cartridge 45 may be constructed from a relatively rigid material, such as a hard plastic or metal, or may be relatively pliable and flexible, such as a plastic bag.

Cartridge 45 further consists of a means to cooperate with the housing during use of the device, to, in turn, allow the volatile substance to be released from the cartridge and to allow air to enter into the cartridge. One such cooperation means comprises cartridge walls 43 that are permeable to ambient air, yet impermeable to the volatile substance contained within the cartridge (as will be described in detail below in reference to FIG. 4). Another cooperation means comprises spikes 48, or other similar means capable of puncturing bottom 44 of cartridge 45, to allow the volatile substance to escape from the cartridge. To this end, a seal, or any material that is easily penetrated, is contemplated for placement over the bottom of the cartridge to prevent escape of the volatile substance before use. Yet another cooperation means consists of top 49 of cartridge 45 being removable, as for instance with the use of a conventional removable seal. Moreover, top 49 may also be puncturable, as for instance by a knife, pen, similar readily available object, or even spikes/puncturing means attached to device top 42. A removable or puncturable top would allow cooperation with a gas generating cell (as will be described hereinbelow in reference to FIG. 8). Of course, one of ordinary skill in the art will understand that numerous other mechanisms for facilitating cooperation between the replaceable cartridge and the housing are likewise contemplated. Cartridge 45 may be removed and replaced after the volatile substance has been released.

Opening 30, shown in FIGS. 1 and 2, may be. of any preferred size. In one preferred embodiment, opening 30 is the size of the inner diameter of housing 22.

Porous plug 33, also shown in FIGS. I and 2, has a top surface 34, bottom surface 36, and is positioned within opening 30 in bottom end 28 of the housing. Although an interference fit is preferred, the porous plug may also be held in the housing by other conventional means such as adhesive, shoulders, fingers, or the like situated on the inner surface of the housing. Because of the orientation of the device, the porous plug is positioned below the volatile substance such that gravity forces volatile substance 21 to come into contact with at least a portion of top surface 34 of the plug. Moreover, in one preferred embodiment, bottom surface 36 of the porous plug is at least partially exposed to the surrounding atmosphere. Furthermore, though the porous plug preferably comprises a microporous polymer membrane, the porous plug may be fabricated from any number of materials including, but not limited to, porous plastic, porous polymers, porous ceramics, porous metals, porous glass, fibrous materials, cellulose, cellulose derivatives, or any combinations thereof.

Figure 12:
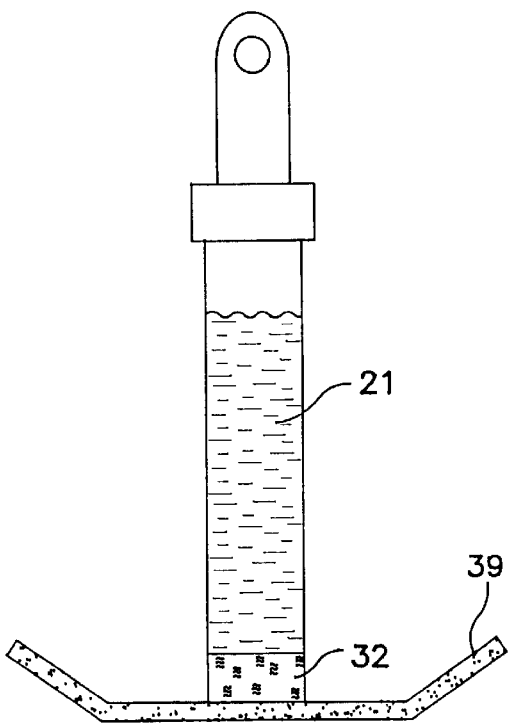
FIG. 12 is a side elevational view of an embodiment of the device in which an emanator pad is associated with the porous plug.

Although bottom surface 36 of porous plug 33 is shown as being partially exposed to the surrounding atmosphere, it is also contemplated that the bottom surface is associated with emanator pad 39 (FIG. 12) to increase the surface area from which volatile substance 21 may evaporate. This increase in evaporation surface area, in turn, allows the release rate of the volatile substance to be increased.

Figure 4:
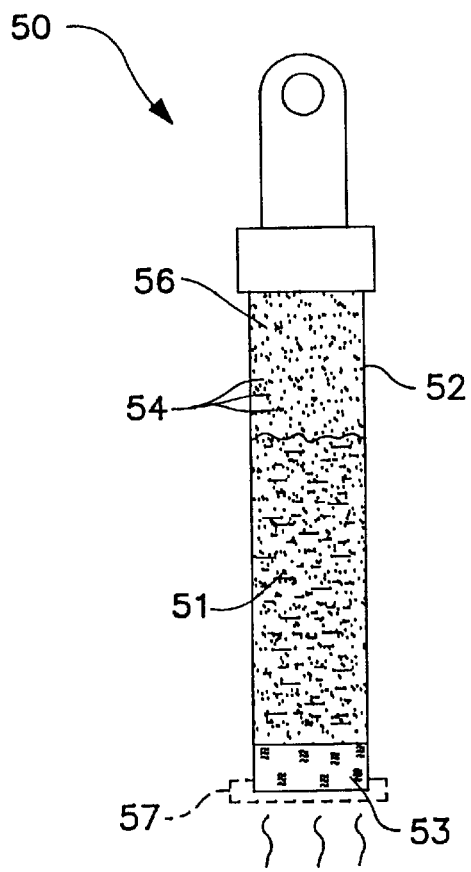
FIG. 4 of the drawings is a side elevational view of an embodiment of the device in which the housing is permeable to ambient air.

Controlled substance release device 50 is shown in FIG. 4 as comprising housing 52, volatile substance 51, porous plug 53, and interior region 56. While the porous plug and volatile substance are similar to those described above in reference to FIGS. 1 and 2, housing 52 is constructed of a material which is substantially permeable to ambient air, but substantially impermeable to the volatile substance contained within the housing. In this embodiment, housing 52, in addition to porous plug 53, serves as the means for controlled release of volatile substance 51.

Specifically, housing 52 consists of a series of microscopic pores 54 which dictate the permeability characteristics of the housing material. To this end, the housing is preferably fabricated from polypropylene, a material that allows the diffusion of ambient air through its pores, but prevents similar diffusion by larger molecules comprising the fragrances, oils, medicines, insecticides, repellents, or the like. Of course, other materials such as high density polyethylene or polyethylene may also be used to fabricate the housing, as they too exhibit favorable permeability characteristics. In such an embodiment, the porosity of housing 52 can be in the range of less than 5 microns to 6 microns. It is also contemplated that only a portion of the housing have pores, or pores of different ranges than the pores located at other portions of the housing. In addition, aside from permeability properties, these housing materials are also selected so as to avoid erosion, decomposition, or abrasion by long term storage of volatile substances. It is also contemplated that in addition to differences in molecule sizes, permeability can be a function of pressure differential, such as a negative pressure within the interior region of the housing as compared to the pressure in the ambient surroundings. In those circumstances, of course, permeability would be a function of the specific characteristics of the particular volatile substance used, as would be understood to one with ordinary skill in the art -- of course entrance of ambient air via mere diffusion through the particular housing material is indeed contemplated.

In operation of device 50, porous plug 53 is sealed before use, preferably by a plastic or metallic material impermeable to both the ambient air and volatile substance 51. Additionally, the ambient air permeable portions of housing 52 may also be sealed by a similar material, however, such a seal is not required. Because the porous plug is sealed, and because the housing is substantially impermeable to the volatile substance, none of the volatile substance escapes from the housing.

Upon removal of the porous plug seal 57, volatile substance 51 becomes capable of diffusing out of housing 52 through porous plug 53. However, any loss of volatile substance 51 from interior region 56 of housing 52 creates a pressure gradient wherein the pressure inside interior region 56 is lower than the pressure in the surrounding atmosphere. This pressure gradient, in turn, builds as more of the volatile substance diffuse through the porous plug, thus hindering the diffusion rate and release rate of the volatile substance from the device.

However, pores 54 in ambient air permeable housing 52 allow air to enter interior region 56 of the housing. The entrance of air at least partially breaks the pressure gradient and allows volatile substance 51 to diffuse through porous plug 53 and to eventually evaporate into the surrounding atmosphere. Moreover, though small amounts of air may enter interior region 56 through porous plug 53, this air endures heavy diffusive resistance from volatile substance 51, which is diffusing through the plug under the force of gravity in the opposite direction. Thus, when compared to the relative ease with which ambient air enters the interior region of the housing through the walls of the housing, any air entering the interior region of the housing through the porous plug has little effect on the rate of release of the volatile substance.

Furthermore, inasmuch as housing 52 is impermeable to volatile substance 51, the volatile substance is prevented from escaping through pores 54 in housing 52. Notably, this feature stands in contrast to other means for breaking the pressure gradient existing between the interior region of the housing and the surrounding atmosphere—for instance a vent in the housing—as those means allow the volatile substance to escape through the housing. This escape of the volatile substance through a passage other than the porous plug is unpredictable and leads to disruption of and inconsistency in the release rate of the volatile substance. Accordingly, the permeability characteristics possessed by housing 52 of device 50 lead to a more uniform, linear, and constant release rate of the volatile substance from the device.

Figure 5:
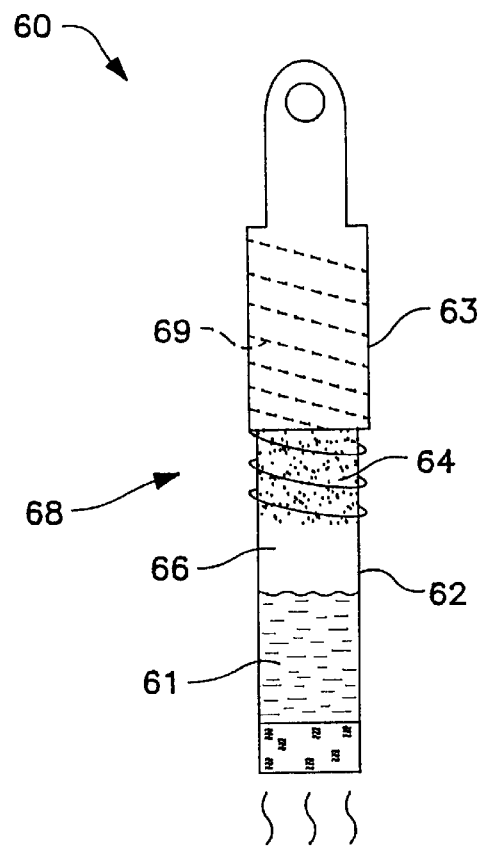
FIG. 5 is a side elevational view of an embodiment of the device in which the user controls the release rate.
Figure 6:
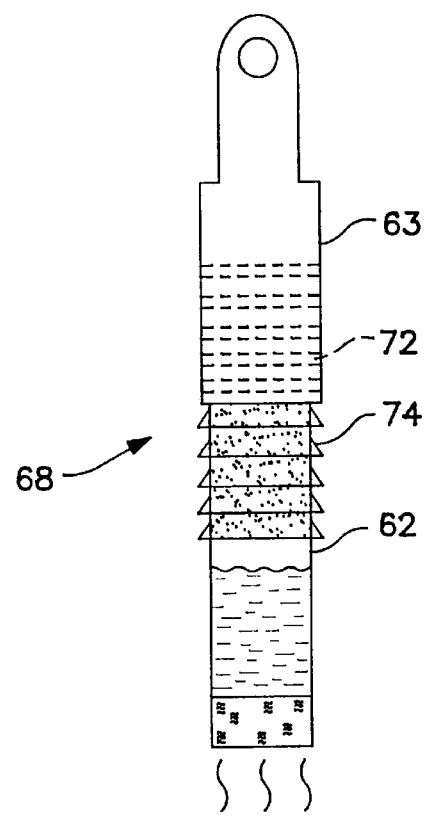
FIG. 6 is a side elevational view of another embodiment of the device in which the user controls the release rate.

Means 68 to control the amount of ambient air entering the interior region of the housing is shown in FIGS. 5–7, wherein controlled substance release device 60 comprises housing 62, volatile substance 61 and interior region of housing 66. In this embodiment, a user of device 60 may selectively control the amount of ambient air entering interior region 66 of housing 62, thus controlling the release rate of volatile substance 61 from the device. Notably, similar to the embodiment described above in reference to FIG. 4, this embodiment contemplates that at least a portion of housing 62 is substantially permeable to ambient air, but substantially impermeable to the volatile substance contained within the housing.

Specifically, ambient air controlling means 68 is shown in FIG. 5 as consisting of housing 62, shell 63, housing threads 64, and shell threads 69 (collectively comprising an adjustable valve). Shell 63 is a separate component from housing 62, and has a larger diameter so as to be positionable over the housing. Housing threads 64 are formed on the outer surface of the housing, and are designated to receive shell threads 69, formed on the inner surface of the shell. When in place, shell 63 selectively obstructs ambient air flow through the ambient air permeable housing walls and into interior region 66. The two sets of threads allow the shell to be adjusted relative to the housing, thus allowing adjustment of the surface area of the air permeable region of the housing exposed to the surrounding atmosphere. Accordingly, adjustment allows either more or less air to enter the interior region of the housing, thus controlling the rate of diffusion of the volatile substance through the porous plug. Additionally, threads 64 and 66 may further consist of detent or locking means (not shown) so as to allow a user to adjust the shell to a number of preset positions.

Ambient air controlling means 68 is also shown in FIG. 6 as comprising a series of corresponding ridges 72 and grooves 74. Ridges 72 are formed on the inner surface of shell 63, while grooves 74 are formed on the outer surface of housing 62. To lock the housing and shell in place, shell 63 snap-fits over housing 62, thus engaging the corresponding ridges and grooves in a fluid-tight seal. Like the threadable assembly described above in reference to FIG. 5, the shell may be moved up or down to selectively adjust the degree of exposure of the air permeable portions of the housing to the ambient air—thus adjusting the amount of air entering the housing and the release rate of the volatile substance. Of course, it will be understood by one of ordinary skill in the art that a reverse construction, with the ridges positioned on the outer surface of the housing and grooves positioned on the inner surface of the shell, is equally viable.

Ambient air controlling means 68 is additionally shown in FIG. 7 consisting of lug 82 and channel 84. Lug 82 is formed on the outer surface of housing 62, while channel 84 is formed on the inside of shell 63. Channel 84 has a number of set lug stops 86, so as to allow the lug to be positioned within the lug stops at preset positions. Again, by adjusting the shell relative to the housing, a user controls the surface area of the ambient air permeable portion of the housing obstructed by the shell, thus controlling the amount of air entering the interior region of the housing. Of course, like the ridge and groove embodiment, a reverse construction is also contemplated.

Although several specific variations of means to control the amount of ambient air which enters into the interior region of the housing have been disclosed, it will be understood to those having ordinary skill in the art that numerous other mechanisms for achieving the same results are likewise contemplated by the present disclosure. Indeed, any of such adjustable mechanisms, by controlling the amount of ambient air that enters into the housing, the user will, in essence, be selectively controlling the amount of volatile substance entering the surrounding atmosphere to, for instance, vary the ambient concentration of a fragrance, medicine, insect repellant, or other volatilizing substance.

Figure 8:
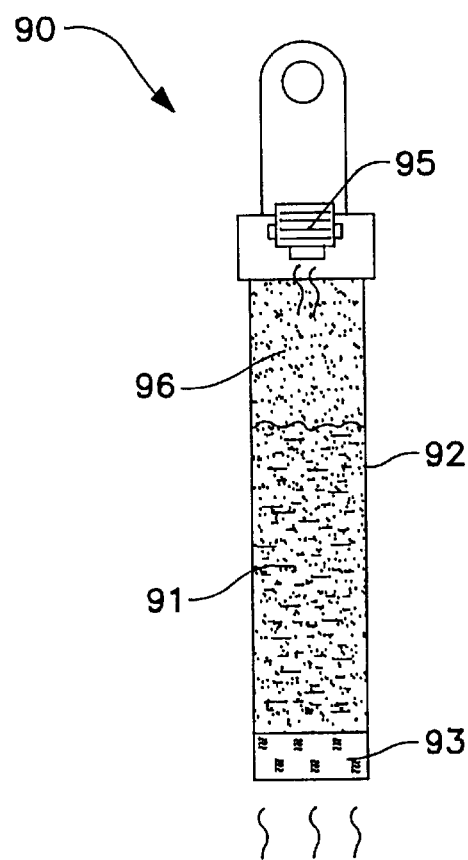
FIG. 8 of the drawings is a side elevational view of an embodiment of the device incorporating a electrochemical gas generating cell.

Controlled substance release device 90 is shown in FIG. 8 as comprising housing 92, volatile substance 91, interior region of housing 96, electrochemical gas generating cell 95, and porous plug 93. Gas generating cell 95 may comprise a conventional gas releasing electrochemical cell such as those disclosed in U.S. Pat. Nos. 5,427,870 and 5,454,922 to Joshi et al., both of which are incorporated herein by reference. Gas generating cell 95 not only assists gravity in dispensing volatile substance 91 through porous plug 93, but gas generating cell 95, in combination with the porous plug, act as the means for controlled release of the volatile substance—toward a linear and constant release of same. Specifically, the gas generating cell is positioned within the device such that gases generated therefrom are emitted into interior region 96 of housing 92. Emission of the gases into the interior region of the housing, in turn, breaks the pressure gradient created by the diffusion of volatile substance 91 through porous plug 93 (described above), thus allowing the volatile substance to diffuse through porous plug 93 at a relatively uniform, linear, and constant rate. Moreover, by controlling the amount of gas emitted by gas generating cell 95, the pressure in the interior region of the housing may be controlled to increase or decrease the rate of diffusion of the volatile substance through the porous plug and, in turn, the rate of volatilization from the porous plug. Of course, it is contemplated that gas generating cell 95 may likewise be used in combination with one or more of the ambient air permeable housing embodiments of FIGS. 4–7, as well as with other embodiments disclosed herein, such as an embodiment with heating elements 123 and 125 (described hereinbelow in reference to FIG. 11), as well as an embodiment which does not use a porous plug.

Figure 9:
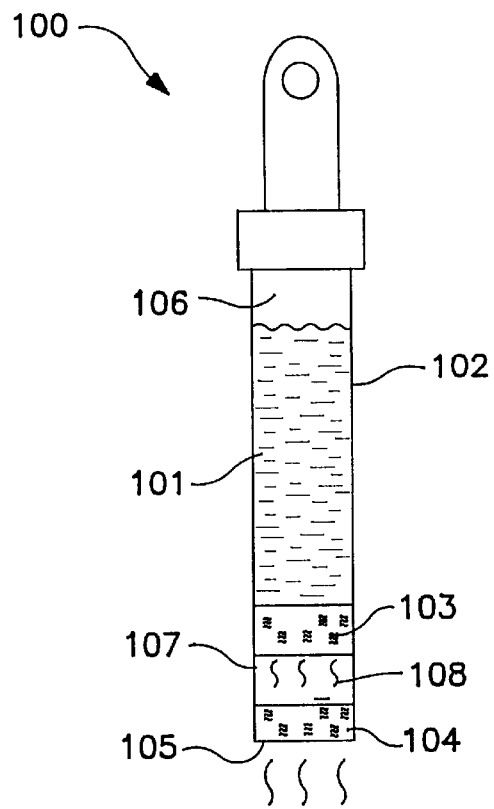
FIG. 9 of the drawings is a side elevational view of an embodiment of the device in which two plugs are separated by an air gap.

Controlled substance release device 100 is shown in FIG. 9 as including housing 102, volatile substance 101, interior region of housing 106, and means 107 for controllably releasing the substance from the housing. Controlled release means 107 consists of first porous plug 103, air gap 108, and second porous plug 104. First porous plug 103 is positioned in interior region 106 of housing 102, and in contact with volatile substance 101. Second porous plug 104 is positioned in the bottom of the housing with at least a portion of its bottom surface 105 exposed to the ambient atmosphere. Air gap 108 is formed between the porous plugs, as no portion of the second porous plug comes into contact with the first porous plug. Although not shown, it is contemplated that the housing is fabricated from a porous medium (such as shown in FIG. 4) and that the portion of the housing surrounding the air gap includes more pores, (or pores of greater size) than the pores in the remainder of the housing.

In operation, volatile substance 101 diffuses through second porous plug 104 and enters air gap 108 between the plugs in a substantially vapor form. The vapor then diffuses through first porous plug 103, before entering the surrounding atmosphere. The use of two porous plugs separated by an air gap controls and linearizes the rate of release of the volatile substance into 106 the ambient atmosphere.

It is contemplated that the porous plugs may have differing porosities and/or dimensions so as to both control the rate of release of the volatile substance and to accommodate the substantially liquid phase encountered by the second porous plug and the substantially vapor phase experienced by the first porous plug. Furthermore, it is also contemplated that at least a portion of the vapor phase entering the first porous plug is converted back into its liquid phase before volatilizing from the bottom of the first porous plug. Of course, it is likewise contemplated that the two plug configuration of this embodiment may be used in combination with the one or more additional features, such as the electrochemical gas generating cell 95 (FIG. 8), heating elements 123 and 125 (FIG. 11), and ambient air permeable housing embodiments (FIGS. 4–7), as well as with a replaceable volatile substance cartridge.

Figure 10:
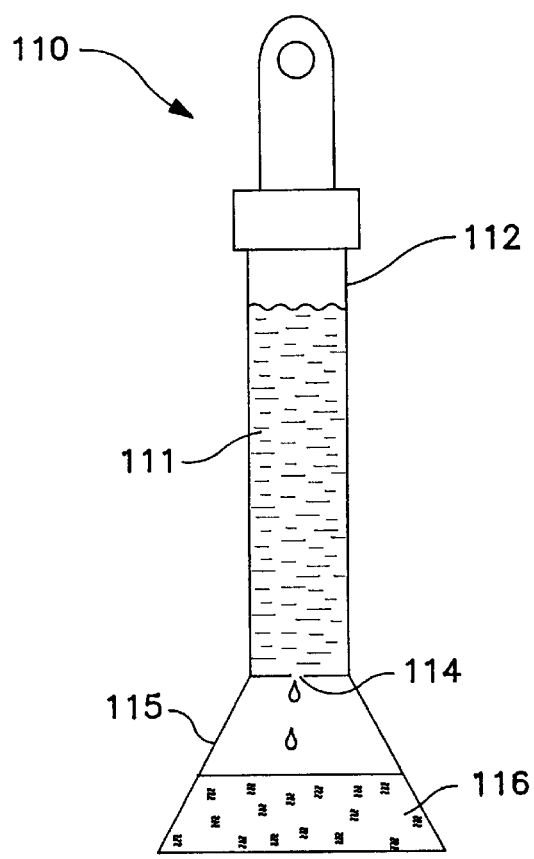
FIG. 10 of the drawings is a side elevational view of another embodiment of the device according to the present invention.

Controlled substance release device 110 is shown in FIG. 10 as comprising housing 112, volatile substance 111, and means 115 for controllably releasing the substance from the housing, which, in the embodiment of FIG. 10, consists of opening 114, and emanator pad 116. Volatile substance 111 is contained in housing 112, which is positioned above opening 114. The opening, in turn, is positioned above emanator pad 116, which is at least partially exposed to the ambient atmosphere. In operation, volatile substance 111 drips liquid through opening 114 and falls onto emanator pad 116 below, where the substance is absorbed by the pad. The volatile substance then evaporates from the surface of the emanator pad into the surrounding atmosphere.

Emanator pad 116 may be placed within the housing, as shown in FIG. 10, or maintained separately from the housing, for instance positioned below the device when the device is in a hanging position. Moreover, it is contemplated that the size of the emanator pad may be varied—thus varying the surface area of the emanator pad exposed to the atmosphere. This variation in surface area, in turn, allows the rate of volatilization of the substance from the emanator pad to be varied—for instance, increasing the surface area of the emanator pad for a greater volatilization rate. Moreover, it is also contemplated that the device of this embodiment may be used in combination with one or more additional features, such as electrochemical gas generating cell 95 (FIG. 8), heating elements 123 and 125, (described hereinbelow in reference to FIG. 11), ambient air permeable housing embodiments (FIGS. 4–7) and a replaceable volatile substance cartridge.

Figure 11:
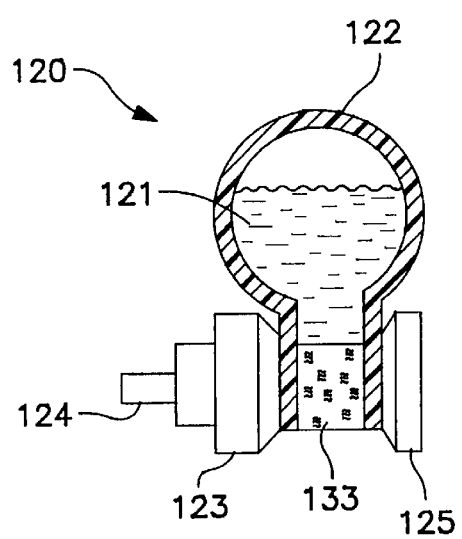
FIG. 11 is a side elevational view of an embodiment of the device in which a heating element is used in combination with the porous plug.

Controlled substance release device 120 is shown in FIG. 11 and consists of housing 122, volatile substance 121, porous plug 133, and heating elements 123 and 125. Preferably, heating elements 123 and 125 are positioned proximately to porous plug 133, so as to allow either the porous plug, or the volatile substance, to be heated. This heating, in turn, increases the volatilization rate of volatile substance 121 from the device. Additionally, device 120 preferably consists of standard wall socket member 124 to activate heating elements 123 and 125, although other conventional heat activating means, such as a battery or other electrical source, are likewise contemplated. Moreover, although a circular housing is shown in FIG. 11, the housing may comprise any desired configuration.

In addition to what has been disclosed, it will be recognized by those of ordinary skill in the art that other features of the controlled substance release device, such as the surface area of the porous plug exposed to the surrounding atmosphere; the physical properties of the plug (ie porosity, material, etc.); the physical properties of the volatile substance; the height of the device; and the diameter or circumference of the device, among others, also dictate the rate of release of the volatile substance. Accordingly, these factors may also be adjusted in combination with one of the above-described embodiments to assist in controlling the rate of release of the volatile substance and to assist in achieving a linear, constant and controlled release rate. Moreover, although the device is shown in the Figures as substantially cylindrical in shape, it is likewise contemplated that the device may take any number of shapes, including circular, spherical, square, rectangular, pyramidal, triangular, polygonal, tubular, or conical, to name just a few.

The foregoing description and drawings merely explain and illustrate the invention and the invention is not limited thereto except insofar as the appended claims are so limited, as those skilled in the art who have the present disclosure before them will be able to make modifications and variations therein without departing from the scope of the invention.

What is claimed is:

1. A device for releasing a volatile substance comprising:
   a housing having an interior region, an outer surface, and an opening in at least one end;
   a volatile substance contained within the interior region of the housing;
   means for orienting the device such that gravity forces the volatile substance toward the opening; and
   means for controllably releasing the volatile substance from the housing, the controlled release means includes means for enabling and controlling the entrance of ambient atmosphere into the interior region of the housing, wherein the ambient atmosphere control and enabling means comprises at least a portion of the housing being constructed from a material which is substantially impermeable to the volatile substance within the interior region of the housing yet substantially permeable to the ambient atmosphere.

2. The device according to claim 1 further including means for controllably diffusing the volatile substance into the ambient environment in a vapor phase.

3. The device according to claim 2 wherein the diffusion means includes at least one porous plug at least partially positioned within the interior region of the housing and associated with the volatile substance.

4. The device according to claim 2 wherein the diffusion means includes an emanator pad associated with at least one of the volatile substance or at least one porous plug.

5. The device according to claim 1 wherein the ambient air control means includes an adjustable valve associated with the housing.

6. The device according to claim 1 further including a gas generating cell associated with the interior region of the housing for controllably assisting in the flow of the volatile substance through the opening in the housing.

7. The device according to claim 1 further including means for heating at least one of the volatile substance or air located within the interior region of the housing.

8. The device according to claim 1 further including means for re-supplying additional volatile substance into the interior region of the housing when desired.

9. The device according to claim 8 wherein the re-supply means comprises a replaceable volatile substance cartridge.

10. The device according to claim 1 further including means for re-supplying additional volatile substance into the interior region of the housing when desired.

11. The device according to claim 10 wherein the re-supply means comprises a replaceable volatile substance cartridge.

12. The device according to claim 10 wherein the controlled release means further includes:
   a first porous plug having a top surface and a bottom surface, wherein at least a portion of the top surface is positioned within the interior region of the housing, and at least a portion of the bottom surface is exposed to ambient atmosphere;
   a second porous plug having a bottom end and a top end wherein the top end is in at least partial contact with the volatile substance contained within the interior region of the housing and the bottom end is facing the top surface of the first porous plug; and
   a gap between the top surface of the first porous plug and the bottom end of the second porous plug.

13. The device according to claim 12 wherein:
   the second porous plug includes means for absorbing or adsorbing a portion of the volatile substance, and, means for releasing the volatile substance into the gap in at least one of a vapor or liquid phase; and
   the first porous plug includes means for absorbing or adsorbing the vapor or liquid phase of the volatile substance from the gap and then for diffusing the volatile substance into the ambient environment in a vapor phase.

14. The device according to claim 13 wherein the absorbing or adsorbing means of the first and second porous plugs comprise the first and second porous plugs being selected from at least one of the group consisting of porous plastic, porous polymers, porous ceramics, porous metals, porous glass, fibrous material, cellulose or cellulose derivatives.

* * * * *